United States Patent [19]

Grove

[11] Patent Number: 4,872,836

[45] Date of Patent: Oct. 10, 1989

[54] RELEASABLE EXTRAORAL ORTHODONTIC APPLIANCE

[76] Inventor: James E. Grove, 6514 Graves Ave., Van Nuys, Calif. 91406

[21] Appl. No.: 721,240

[22] Filed: Apr. 8, 1985

[51] Int. Cl.$^4$ ............................................. A61C 7/00
[52] U.S. Cl. ...................................................... 433/5
[58] Field of Search ............................................ 433/5

[56] References Cited

U.S. PATENT DOCUMENTS

4,215,983 8/1980 Frazier .................................. 433/5
4,226,589 10/1980 Klein ..................................... 433/5
4,238,188 12/1980 Armstrong .............................. 433/5

Primary Examiner—Robert Peshock
Attorney, Agent, or Firm—Jack C. Munro

[57] ABSTRACT

An extraoral orthodontic force applying appliance defining an encircling assembly to be located about the head of the wearer which includes a single release mechanism incorporated at the nape of the wearer which will separate the encircling assembly upon the encircling assembly incurring an unusual force tending to enlarge the enclosed area of the encircling assembly. This release mechanism can be also purposely manually operated by the wearer for connection and disconnection. The encircling assembly can be collapsed when not in use to facilitate storage and portability.

6 Claims, 5 Drawing Sheets

RELEASABLE EXTRAORAL ORTHODONTIC APPLIANCE

BACKGROUND OF THE INVENTION

The field of this invention relates to orthodontic headgear and more particularly to a safety-release, tension applying mechanism for use about the head of an individual for applying force to the teeth of the individual through teeth mounted braces for the purpose of achieving proper occlusion.

Within orthodontics it is common to use extraoral (outside of the mouth) devices to apply a steady continuous force to intraoral (inside of the mouth) devices for the purpose of assisting in obtaining or maintaining of proper occlusion. Orthodontics is most commonly utilized in conjunction with children. In conjunction with an extraoral orthodontic appliance, in the past it has been a frequent occurrence for one child to grab onto such an appliance of another child during play or other social activity.

Such extraoral orthodontic equipment inherently must incorporate some means to connect to the intraoral orthodontic equipment. The means of connection usually involves sharp pointed objects to minimize the size of the structure which enters the mouth of the wearer. The smaller the object entering the mouth, the less interfering the object is to normal activity of the mouth. However, upon the child grabbing and pulling on another child's extraoral orthodontic equipment causing disengagement with the intraoral orthodontic equipment, if that extraoral equipment remains intact and the child then releases such, a snapback occurs which can cause the sharp pointed portions of the extraoral orthodontic equipment to injure the wearer in the area of the face. In the past, multitudes of serious injury have occurred.

The reason for the snapback is that, inherently with such orthodontic equipment, there is incorporated a spring assembly. The function of the spring assembly is to apply a spring force through the extraoral orthodontic equipment to the intraoral orthodontic equipment. When the extraoral orthodontic equipment is disengaged from the intraoral orthodontic equipment, this spring force is capable of forcibly moving the sharp pointed sections of the extraoral orthodontic equipment into contact with the wearer's face to cause the injury.

In the past, it has been common to design a release mechanism in conjunction with extraoral orthodontic equipment. The function for the release mechanism is that, if the extraoral orthodontic equipment is disengaged from the intraoral orthodontic equipment, the extraoral orthodontic equipment will physically break apart thereby preventing snapback and injury to the wearer. Previously, common forms of such releasable extraoral orthodontic equipment have been defined within U.S. Pat. Nos. 4,115,921; 4,155,161; 4,215,983; 4,226,589; 4,238,188; 4,368,039; 4,402,669; and 4,416,625. These previous release mechanisms, in most instances, satisfactorily satisfy the requirement to effect breaking apart or in some manner negating the tension producing force included within the orthodontic headgear when such headgear encounters an unusual pulling force of a sufficient predetermined amount. However, these mechanisms in the past have proved to be complex in construction since such are composed of many parts and inherently are expensive to manufacture.

Additionally, extraoral orthodontic equipment is not worn by the wearer at all times. Usually, several times during any given day, the wearer will remove the appliance and locate such in a pocket or purse for a period of time before it is reinstalled in position. In the past, the extraoral orthodontic appliances have not been designed to facilitate ease of removal and reinstallation. Additionally, such extraoral orthodontic appliances have not been designed to be collapsible so as to occupy a small space to facilitate location within one's pocket or purse.

SUMMARY OF THE INVENTION

The structure of the present invention is directed to an extraoral orthodontic appliance which basically defines an encircling assembly composed of a facebow which is connected at each side thereof to yieldable force applying sections which in turn are connected together through a disconnection assembly which is to be mounted against the nape or the back of the head of the wearer. The disconnection means takes the form of a separable male and female member assembly which is designed to be operated either by choice or upon the encircling assembly incurring an unusual outward force of a predetermined or greater amount. The connection of each of the side sections to the disconnection assembly is such that each side section is capable of being moved toward each other to achieve collapsing of the device to faciliate stowage and portability when not in use.

The primary objective of the present invention is to provide a non-complex extraoral orthodontic appliance which can quickly and easily separate from the intraoral orthodontic appliance upon experiencing a small amount of outward pulling force.

Another objective of the present invention is to construct an extraoral orthodontic appliance which can be quickly and easily removed and reinstalled by individuals and particularly children.

Another objective of the present invention is to provide an extraoral orthodontic appliance which can be quickly and easily adjusted to accommodate patients of different head size.

Another objective of the present invention is to constuct an extraoral orthodontic appliance which can be readily collapsed into a relatively small size for stowage purposes when not in use.

Another objective of the present invention is to construct an extraoral orthodontic appliance which can be manufactured inexpensively and, therefore, sold to the consumer inexpensively.

DETAILED DESCRIPTION OF THE SHOWN EMBODIMENT

Referring particularly to the drawings, there is shown the orthodontic appliance 20 of this invention which is composed generally of a front section 22 and a rear section 24. The front section 22 and rear section 24 are connected together by side sections 26 and 28. Each of the side sections 26 and 28 are basically identical in construction and it is to be understood that further on in this specification that the discussion to one of the side sections will apply similarly to the other side section.

Front section 22 is what is frequently called a facebow. The facebow 22 is designed to include an outer bow 30 and an inner bow 32. The central section of the inner bow 32 is integrally connected to the central portion of the outer bow 30. Normally, the inner bow 32 and the outer bow 30 will be constructed of a material such as plastic or metal with generally a metal type of rod being preferable.

The inner bow 32 terminates at its ends into a pair of spaced-apart tips 34. The tips 34 are to engage with the intraoral orthodontic appliance (not shown) which is to be worn on the teeth of the wearer 36. The free outer ends of the outer bow 30 are formed into hooks 38 and 40.

Hook 40 is to be connectable within any one of a series of holes 42 formed within a strap 44. The holes 42 are evenly spaced apart and each include identifying numerical indicia 46. The indicia 46 is to assist the user and the orthodontist installing the hook 40 at a desired location for a particular size of wearer 36. In other words, the holes 42 permit adjustability of the orthodontic appliance 20 of this invention so that the appliance 20 will accommodate all sizes of individuals from small children to adults.

It is to be understood that a strap 48, which is basically identical to strap 44, is to connect to hook 38. Included within the strap 48 are holes 50 which are similar to holes 42. The straps 44 and 48 will normally be constructed of plastic material with polypropylene being preferred. For purposes of this invention, the portion of the orthodontic appliance 20 that is located between straps 44 and 48 and in contact with the nape of the wearer shall be generally referred to as a neckband.

Figure 7:
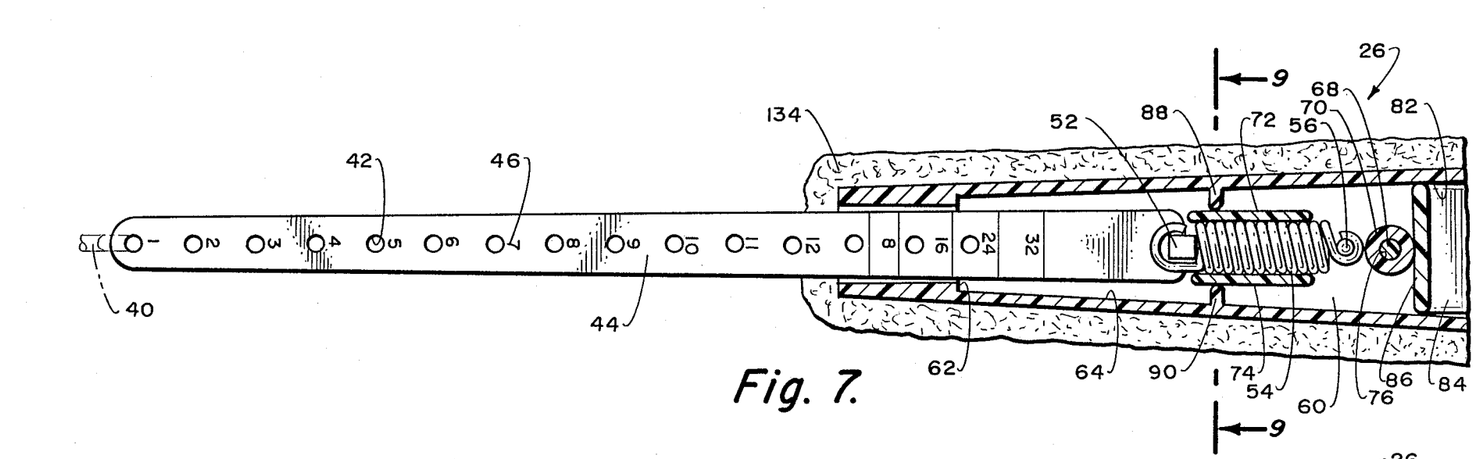
FIG. 7 is a cross-sectional view through one of the side sections of the extraoral orthodontic appliance of the present invention taken along line 7—7 of FIG. 6, showing the spring force applying device of the side sections in the retracted position.
Figure 8:
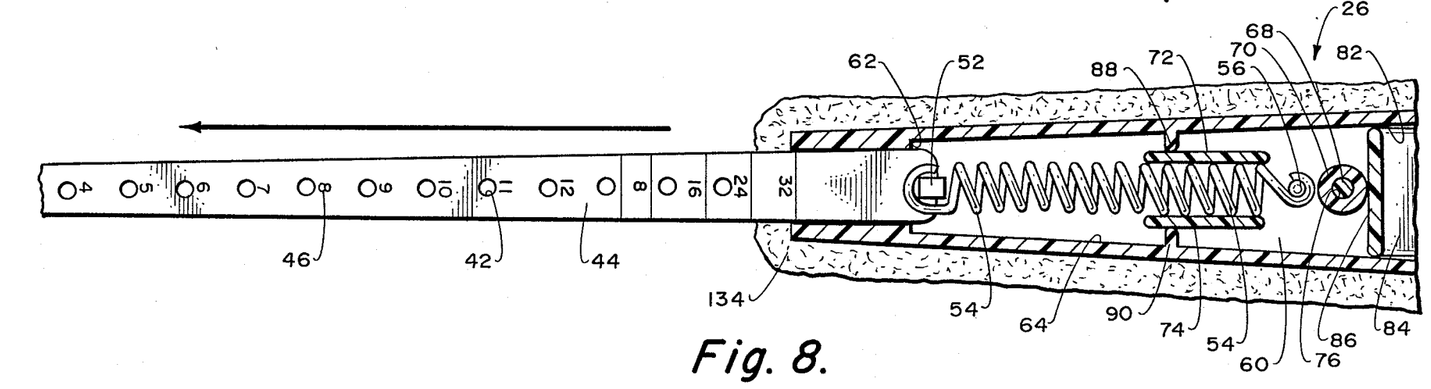
FIG. 8 is a view similar to FIG. 7, but showing the spring force applying device in the extended position.

The inner end of the strap 44 includes an upstanding protuberance 52. Connecting with the protuberance 52 is one end of a coil spring 54. The opposite end of the coil spring 54 connects to a fixed protuberance 56. The fixed protuberance 56 is integrally mounted on the inner surface 60 of a backplate 58. The inside wall surface of the protuberance 52 abuts and continuously remains against the inner surface 60. Actually, the protuberance 52 rides (moves) along inner surface 60 from a retracted position shown in FIG. 7 to an extended position shown in FIG. 8.

With the protuberance 52 in the extended position, a portion of the protuberance 52 will abut against shoulder 62 of the backplate 58. The inner end of the strap 44 is contained within a chamber 64 formed between the backplate 58 and an outer plate 66. Outer plate 66 will normally be secured to the backplate 58 by means of an interlocking fitting of backplate 58 with outer plate 66.

In order to hold the coil spring in position, there is integrally mounted on the backplate 58, and extending upward in a spaced apart arrangement within the chamber 64, a pair of guide rails 72 and 74. To assist in securing together the plates 58 and 66, there is utilized a protuberance 68 which is integrally mounted on the backplate 58 and which is to snugly fit within recess 76 formed within the protuberance 70. Protuberance 70 is integrally formed onto the outer plate 66. When protuberance 68 is located within recess 76, the outer plate 66 is locked tightly to backplate 58.

To further assist in correctly aligning together of the plates 58 and 66 when connected together, aside from the snug fit between protuberance 68 and recess 76, there is utilized lateral protuberances 88 and 90 which are integrally mounted on the inside surface of the outer plate 66. The protuberances 88 and 90 are located within the inner chamber 64. Protuberance 88 is to abut against guide rail 72. Protuberance 90 is to abut against guide rail 74.

Figures 6, 9, 12:
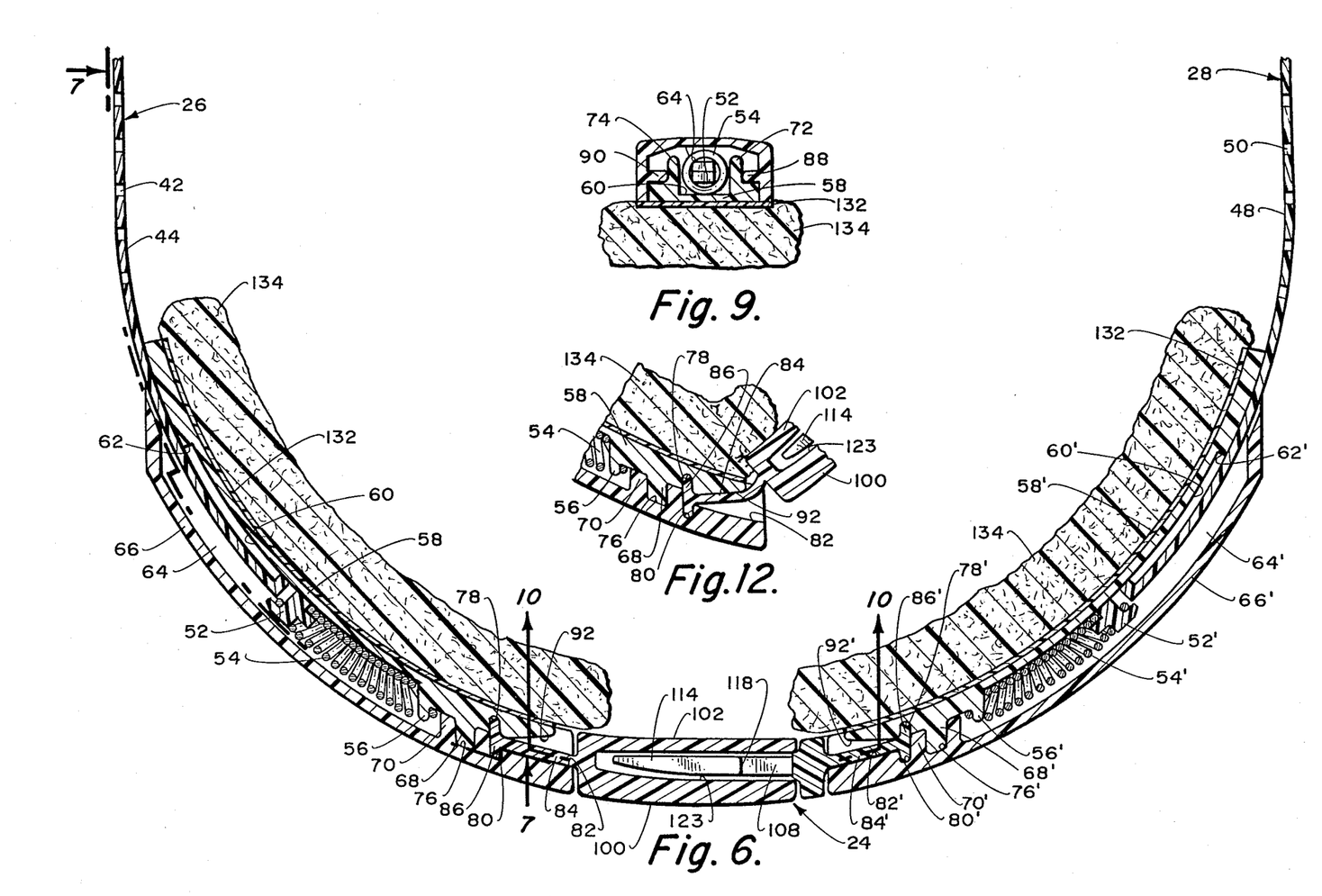
FIG. 6 is a cross-sectional view taken along line 6—6 of FIG. 4.
FIG. 9 is a cross-sectional view of a side section through the spring force applying device taken along line 9—9 of FIG. 7.
FIG. 12 is an enlarged cross-sectional view showing the flexing of the orthodontic appliance of this invention for the purpose of collapsing of such to facilitate stowage when not in use.

Formed within the backplate 58 is a lineal groove 78. A similar groove 80 is formed within the front plate 66 and is in substantial alignment with the groove 78. Connecting the aligned pair of grooves 78 and 80 is a longitudinal slot 82. The longitudinal slot 82 is of a size so that a flexible band 84 can be located therewithin. The band 84 is integrally connected at one end thereof to an elongated double headed protuberance 86. The protuberance 86 is of a size to fit closely within aligned grooves 78 and 80. The portion of the slot 82 which is formed by the front plate 66 is basically planar. The portion of the slot 82 which is formed by the backplate 58 is arcuate forming arcuate surface 92. Basically, a portion of the inner plate has been removed providing for an area of movement of the band 84 between arcuate surface 92 and outer plate 66. As a result, the bank 84 can be moved within the slot 82 from the position shown in FIG. 6 to the position shown in FIG. 12 of the drawings. This flexing movement is such that the entire side section 26 can be moved to decrease the size of the enclosed area defined by the encircling orthodontic appliance 20. This flexing movement is to facilitate collapsing of the orthodontic appliance 20 so that appliance 20 can be conveniently stored when not in use. The flexing movement also facilitates adjustment to the wearer when in use.

It is to be understood that the band 48 is connected in essentially an identical manner to a coil spring 54' through a protuberance 52'. The protuberance 52' is mounted against inner wall 60' of a backplate 58'. Between the backplate 58' and the outer plate 66' there is located a chamber 64'. One end of the coil spring 54' is also connected to protuberance 56'. A protuberance 68' fits in a close fitting manner within a recess 76'. Recess 76' is formed within protuberance 70'. Band 84' is mounted within slot 82'. The inside surface of slot 82' is formed by arcuate wall 92'. The inner end of the band 84' terminates in a double headed protuberance 86'. The protuberance 86' is mounted between aligned grooves 78' and 80'.

It is to be understood that the material of construction of the bands 84 and 84' will be of a plastic material. Actually, for purposes of this invention, it is to be understood that, all parts of the orthodontic appliance 20 of this invention will be constructed of a plastic material with a possible exception of the facebow 22 and springs 54 and 54'.

The disconnection assembly 24 includes a female coupling member defined by recess 94 formed within the outer portion of the band 84 and an opening 96 formed within extension 98. Extension 98 is integrally connected to band 84 by means of a pair of spaced apart parallel webs 100 and 102. Outwardly formed on each side of the webs 100 and 102, in between the extension 98 and the band 84, are cutout openings 104 and 106.

Integrally connected to the band 84' and extending therefrom are a pair of closely spaced apart arms 108 and 110. Each of the arms 108 and 110 assume a basically pointed configuration having an outer rounded tip. In between the arms 108 and 110 is located an enlarged gap area 112.

Arm 108 has a lateral exterior inclined surface 114. Similarly, arm 110 has a lateral exterior inclined surface 116. The aft end of the surface 14 terminates in a cam surface 118. In a similar manner, the inclined surface 116 terminates at its aft end into a cam surface 120.

The arms 114 and 116 are to be inserted in the space 123 formed between webs 100 and 102. During insertion, the inclined surfaces 114 and 116 will ride against their respective surfaces of the opening 96 causing the arms 108 and 110 to deflect partially closing of gap area 112. This is clearly shown within FIG. 11 of the drawings. As the arms 108 and 110 are continued to be inserted until finally the tips of the arms rest within recess 94, the arms 108 and 110 will naturally spread apart to the position shown in FIG. 10. In this position the web 84' is secured to web 84 with the orthodontic appliance 20 forming a continuous encircling member.

If unusual force is applied, as by a person's hand 121 to the facebow 22, initially the straps 44 and 48 will move to the extended position stretching of their respective coil springs 54 and 54'. The direction of this extending movement is shown by the arrows 122 and 124 within FIG. 2 of the drawings. This extending movement continues until protuberance 52 abuts shoulder 62 and protuberance 52' abuts shoulder 62'. At this time, further relative movement of the straps 44 and 48 relative to plates 58 and 58' is now prevented.

Further outward movement of the facebow 22 will result in the tips 34 being fully disengaged from the intraoral orthodontic appliance and also will cause the arm 108 to deflect inwardly by the extension 98 being moved up cam surface 118. In a similar manner, the arm 110 is deflected inwardly by the extension 98 by moving along cam surface 120. It is to be noted that the amount of force that is required to achieve the complete deflecting of the arms 108 and 110 will normally be between five and ten pounds, with probably an eight pound force being preferred.

Upon the arms 108 and 110 being positioned within the opening 96, the arms 108 and 110 are then free to be conducted, without hinderance, exteriorly of the opening 96 resulting incomplete separation of the male coupling member, represented by arms 114 and 116, from the female coupling member, represented by extension 98 and webs 100 and 102. Therefore, at this time, snapback of the orthodontic appliance toward the individual 36 is prevented.

Figure 1:
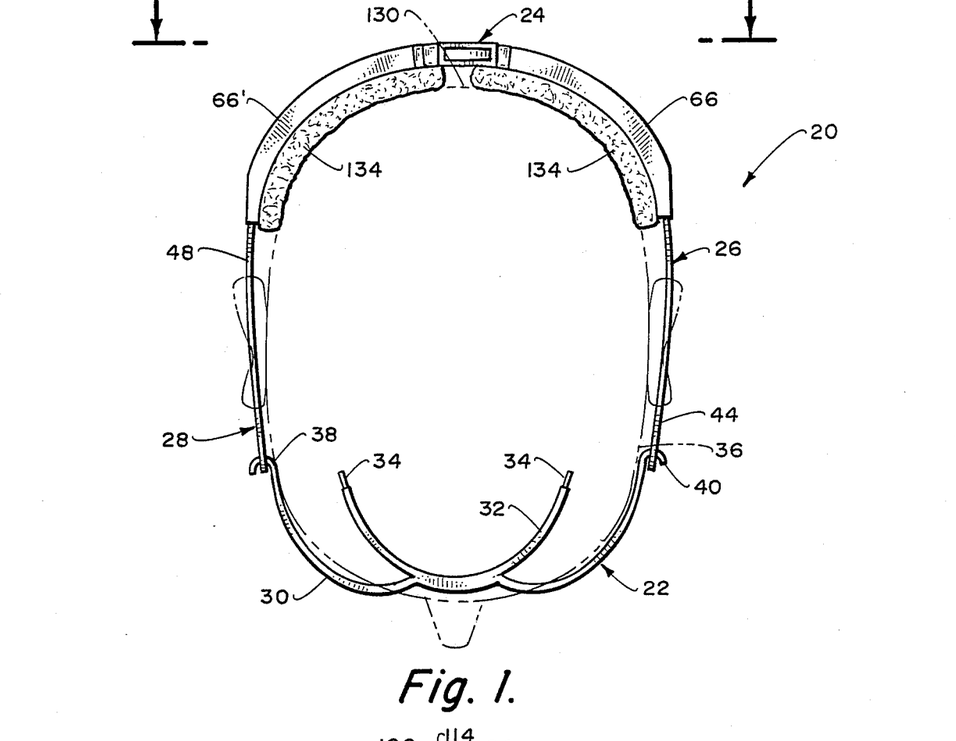
FIG. 1 is a top plan view of the extraoral orthodontic appliance of the present invention showing the appliance as it would be in its normal installed position about the head of an individual in its use position.
Figures 2, 10:
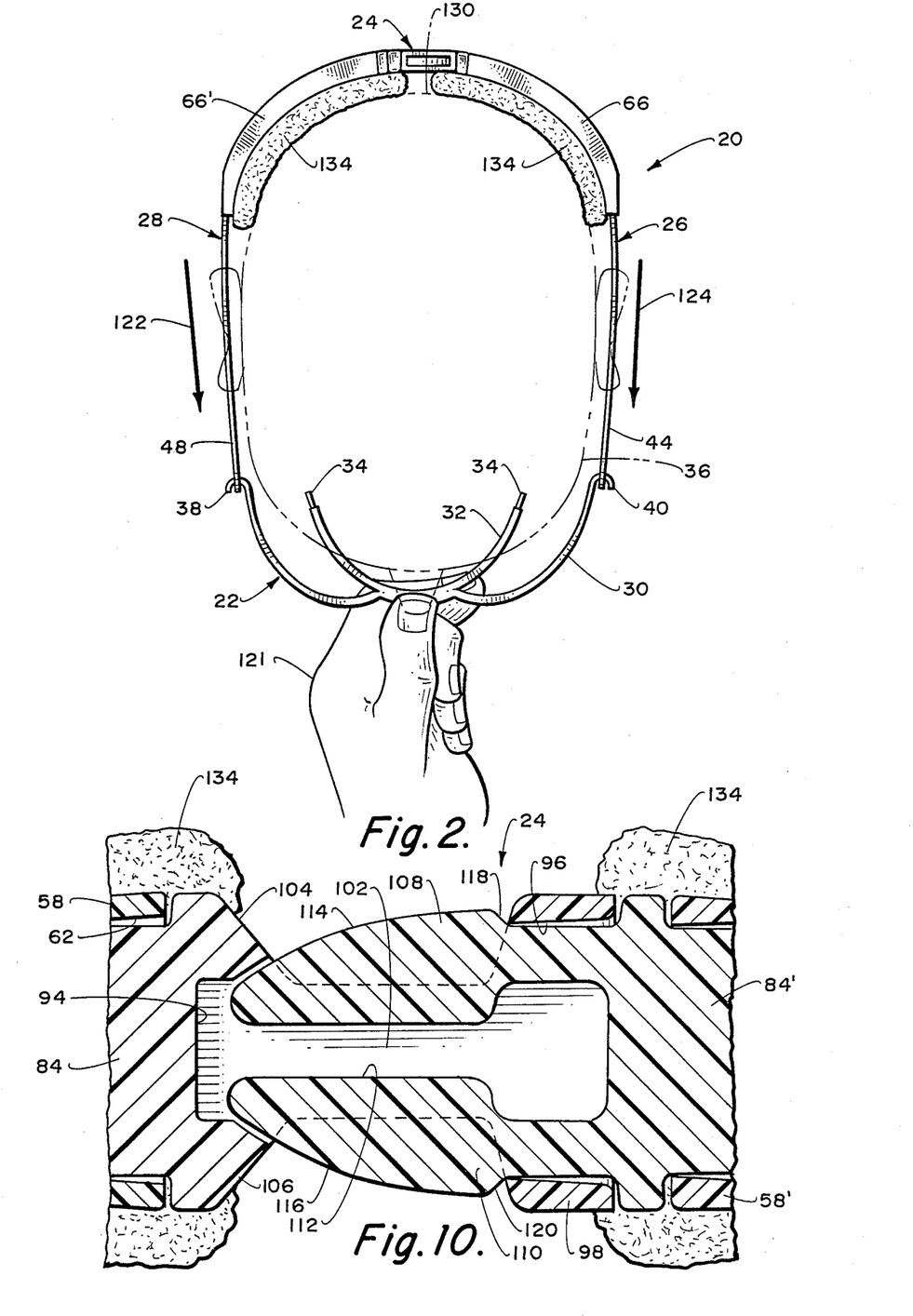
FIG. 2 is a view similar to FIG. 1, but showing the appliance incurring a typical outward pulling force sufficient to locate the appliance in an extended position but with the disconnection assembly still intact.
FIG. 10 is a cross-sectional view through the disconnection assembly taken along line 10—10 of FIG. 6, showing the disconnection assembly in the connected position.
Figures 3, 11:
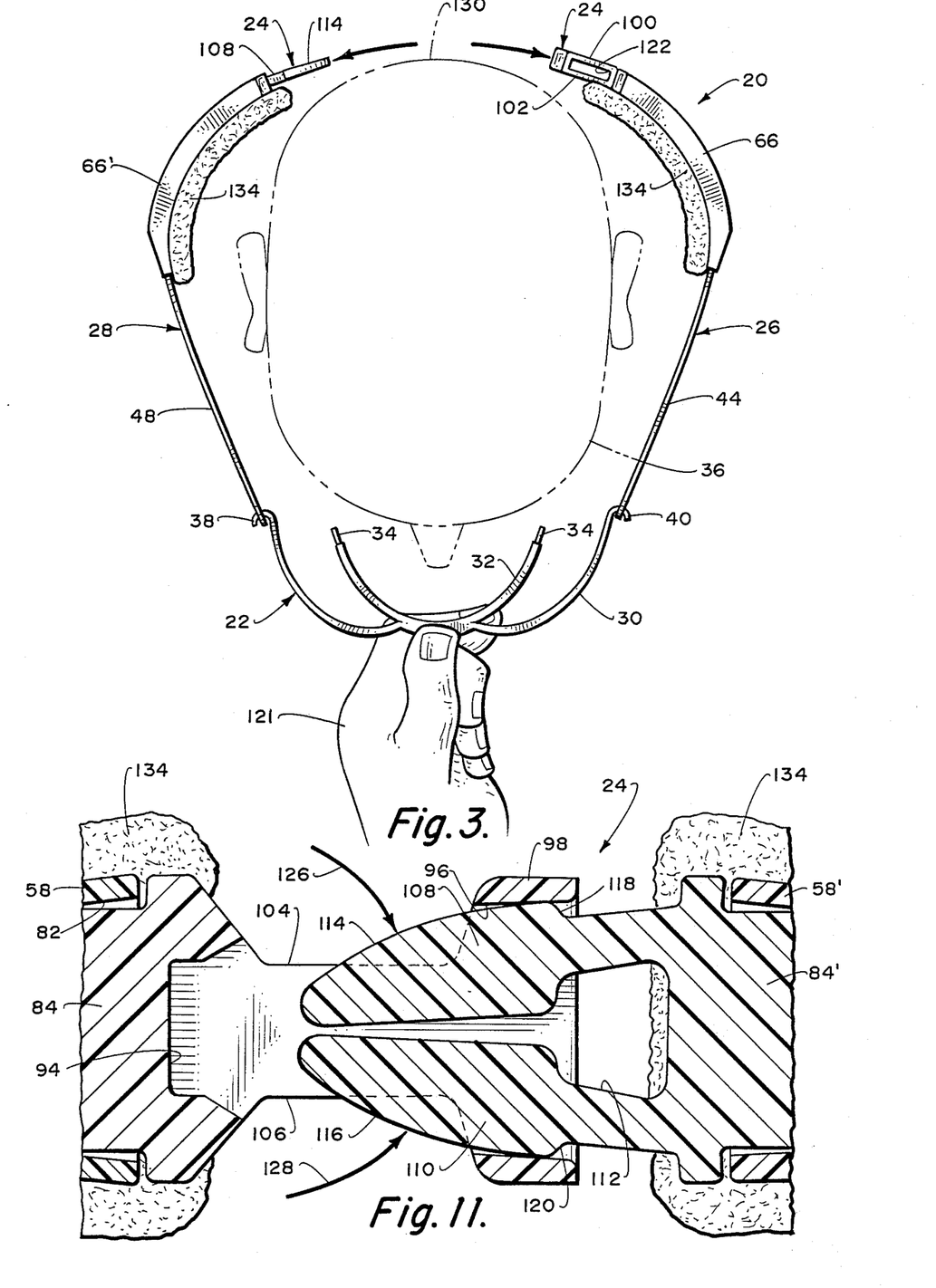
FIG. 3 is a view similar to FIG. 2, but further showing the disconnection assembly in the disconnected position.
FIG. 11 is a view similar to FIG. 10, but showing the disconnection assembly in an intermediate disconnecting position.
Figure 4:
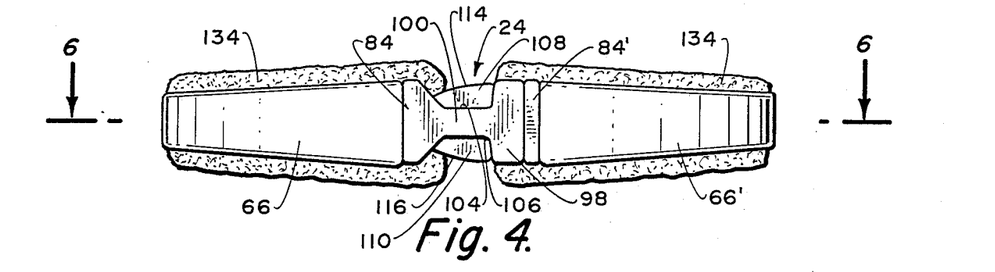
FIG. 4 is a back view of the extraoral orthodontic appliance of the present invention taken along line 4—4 of FIG. 1, showing the disconnection assembly in the connected position.
Figure 5:
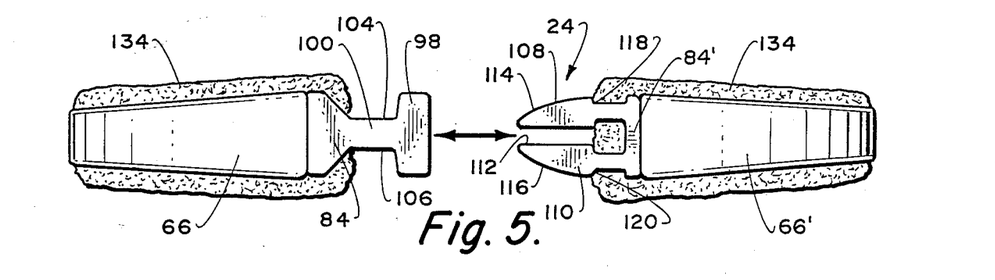
FIG. 5 is a view similar to FIG. 4, but showing the disconnection assembly in the disconnected position.

To reinstall the orthodontic appliance 20 into position, it is only necessary for the wearer to reconnect the tips 34 to the intraoral orthodontic appliance and then manually move arms 108 and 110 through opening 96 until they again reach the position shown in FIG. 10 of the drawings.

The wearer 36 can also disengage the disconnection assembly 24 without pulling outward on the facebow 22. The wearer only need to pinch by applying pressure onto both surfaces 114 and 116 simultaneously causing deflection of the arms 108 and 110 and disengaging of the cam surfaces 118 and 120 from the extension 98 permitting the male coupling member to be removed from the female coupling member. Any application of force (depicted by arrows 126 and 128 in FIG. 11) to the surfaces 114 and 116 will have a natural tendency to disengage the male coupling member from the female coupling member because of the arcuate angle of inclination of surfaces 114 and 116. For reasons of comfort, when the orthodontic appliance 20 is installed about the nape 130 of the wearer 36, it would normally be desirable to adhesively secure strips of foam 134 by means of adhesive strips 132.

Desirable material of construction of arms 108 and 110, webs 84, 84', 100 and 102, and extension 98 is polymethylene ether commonly sold under the tradename of DELRIN. Desirable material for backplates 58 and 58' is ABS and polypropylene for outer plates 66 and 66'.

What is claimed is:

1. An orthodontic appliance adapted to be located about the head of an individual for applying force to the teeth of the individual through teeth mounted braces for the purpose of achieving proper occlusion, said orthodontic appliance comprising:

an encircling assembly adapted to be located about the head of the individual, said encircling assembly being generally composed of a front section and a rear section which are connected together by side sections;

said front section including connecting means for facilitating connection to the teeth mounted braces;

said rear section to be located at the back of the head of the individual, said rear section including a single disconnection means which disconnects upon applying of a predetermined amount of force to said front section in a direction away from said rear section;

each said side section being extendible in length from a retracted position to an extended position upon application of said predetermined amount of force, each said side section including resilient means, said resilient means applying a force to said front section tending to locate said side sections in said retracted position;

said disconnection means comprises a separable coupling device composed of a male member and a female member, said male member including release means which is activated upon said predetermined amount of force being reached;

said release means comprising a cam assembly, said cam assembly being capable of causing deflection of said male member to effect separation of said male member from said female member; and said coupling device further including deflection means for a second way to separate said male and female members, said deflection means comprising a pair of arms formed on said male member, each said arm connecting with a cutout opening formed in said female member, said cutout openings permitting direct manual contact with said arms to cause deflection of said arms toward each other to also result in separation of said male member from said female member.

2. An orthodontic appliance adapted to be located about the head of an individual for applying force to the teeth of the individual through teeth mounted braces for the purpose of achieving proper occlusion, said orthodontic appliance comprising:

an encircling assembly adapted to be located about the head of the individual, said encircling assembly being generally composed of a front section and a rear section which are connected together by side sections;

said front section including connecting means for facilitating connection to the teeth mounted braces;

said rear section to be located at the back of the head of the individual, said rear section including a single disconnection means which disconnects upon applying of a predetermined amount of force to said front section in a direction away from said rear section;

each said side section being extendible in length from a retracted position to an extended position upon application of said predetermined amount of force, each said side section including resilient means, said resilient means applying a force to said front section tending to locate said side sections in said retracted position; and said encircling assembly defining an enclosing area, said encircling assembly including flexing means, said flexing means permitting movement of each said side section relative to said rear section for decreasing the size of said enclosing area to be adjustable to accommodate to various sizes of necks of individuals when in use and also to facilitate collapsing of said encircling assembly when not in use for easy portability, said flexing means comprising a pair of separate thin, bendable, strips of material, a said strip of material located between said single disconnection means and each said side section.

3. An extraoral orthodontic force applying assembly comprising:

a facebow adapted to engage with an intraoral orthodontic appliance;

a neckband adapted to be located against the nape of the wearer;

a pair of extendible tension producing mechanisms connected between said facebow and said neckband, said neckband and said facebow when connected with said tension producing mechanisms producing a ring-shape defining an enclosed area;

a release mechanism sensitive to an unusual force tending to pull apart said facebow and said neckband, activation of said release mechanism causes separation of said neckband into a first part and a second part, said release mechanism being mounted within said neckband; and collapsing means for permitting moving of said assembly to decrease the size of said enclosed area to therefore be adjustable to accommodate to various sizes of necks of wearers when in use and also to facilitate storage and portability when not in use, said collapsing means comprising a pair of separate thin, bendable, strips of material, a said strip of material located between said release mechanism and one of said extendible tension producing mechanisms with the remaining said strip of material located between said release mechanism and the other said tension producing mechanism.

4. An extraoral orthodontic force applying assembly comprising:

a facebow adapted to engage with an intraoral orthodontic appliance;

a neckband adapted to be located against the nape of the wearer;

a pair of extendible tension producing mechanisms connected between said facebow and said neckband, said neckband and said facebow when connected with said tension producing mechanisms producing a ring-shape defining an enclosed area;

a release mechanism sensitive to an unusual force tending to pull apart said facebow and said neckband, activation of said release mechanism causes separation of said neckband into a first part and a second part, said release mechanism being mounted within said neckband;

said release mechanism comprising a separable coupling device composed of a male member and a female member, said male member being deflectable relative to said female member from an at rest position to a deflected position, with said male member in said at rest position said female member and said male member being securely connected together, with said male member in said deflected position said male member being readily movable relative to said female member; and said male member being movable to said deflected position not only upon said release mechanism incurring said unusual force but also by purposely manually moving said male member to said deflected position, said male member including a pair of arms, access opening means provided within said female member for permitting direct physical contact with said arms for deflecting said arms toward each other and into said deflected position.

5. An orthodontic appliance adapted to be located about he head of an individual for applying force to the teeth of the individual through teeth mounted braces for the purpose of achieving proper occlusion, said appliance comprising:

an encircling assembly adapted to be located about the head of the individual, said encircling assembly defining an enclosed area, said encircling assembly including means for permitting moving of said encircling assembly to a position decreasing the size of said enclosed area;

said means for decreasing the size of said enclosed area comprising a pair of thin, bendable, strips of material each movably mounted within a separate enlarged cavity; and said encircling assembly including a disconnection means adapted to be located directly adjacent the nape of the individual, side sections extending from said disconnection means with said disconnection means located between said side sections, a said strip of material being located between each said side section and said disconnection means.

6. An orthodontic appliance adapted to be located about the head of an individual for applying force to the teeth of the individual through teeth mounted braces for the purpose of achieving proper occlusion, said orthodontic appliance comprising:

an encircling assembly adapted to be located about the head of the individual, said encircling assembly being generally composed of a front section and a rear section which are connected together by side sections;

said front section including connecting means for facilitating connection to the teeth mounted braces;

said rear section to be located in the area of the back of the head of the individual, said rear section including a single disconnection means which disconnects upon applying of a predetermined amount of force to said front section in a direction away from said rear section, said disconnection means comprises a separable coupling device composed of a male member and a female member, said male member including release means which is activated upon said predetermined amount of force being reached, said release means including a pair of arms mounted on said male member, said arms being exteriorly exposed by connecting with cutout openings formed in said female member, said release means also being capable of being manually operated by pinching of said arms until said arms are moved a sufficient amount toward each other permitting separation of said male member and said female member; and each said side section being extendible in length from a retracted position to an extended position upon application of a predetermined amount of force, each said side section including a spring applying a force to said front section tending to locate said side sections in said retracted position.

* * * * *